(12) United States Patent  
Srinivasan et al.

(10) Patent No.: US 8,101,422 B2  
(45) Date of Patent: Jan. 24, 2012

(54) MULTIDIMENSIONAL CHROMATOGRAPHY APPARATUS AND METHOD

(75) Inventors: Kannan Srinivasan, Tracy, CA (US); Rong Lin, Santa Clara, CA (US)

(73) Assignee: Dionex Corporation, Sunnyvale, CA (US)

( * ) Notice: Subject to any disclaimer, the term of this patent is extended or adjusted under 35 U.S.C. 154(b) by 1319 days.

(21) Appl. No.: 11/229,002

(22) Filed: Sep. 16, 2005

(65) Prior Publication Data

US 2007/0065343 A1    Mar. 22, 2007

(51) Int. Cl.  
*G01N 30/02* (2006.01)  
*G01N 30/00* (2006.01)

(52) U.S. Cl. .......... 436/161; 422/70; 210/294; 210/659; 210/198.2; 210/635; 210/656; 210/243; 205/789

(58) Field of Classification Search ............ 436/161; 422/70; 210/294, 659, 198.2, 635, 656, 243; 205/789  
See application file for complete search history.

(56) References Cited

U.S. PATENT DOCUMENTS 5,248,426 A  *  9/1993  Stillian et al. ................ 210/635

FOREIGN PATENT DOCUMENTS

EP            0038720 A1    10/1981

OTHER PUBLICATIONS

Bruno, P., et al., "Determination of nutrients in the presence of high chloride concentrations by column-switching ion chromatography," *J. Chromatogr. A* 1003(1-2):133-141 (Jun. 2003).

Columbini, S., et al., "Use of column-switching ion chromatography for the simultaneous determination of total nitrogen and phosphorus after microwave assisted persulphate digestion," *J. Chromatogr. A* 822(1):162-166 (Sep. 1998).  
Galceran, M., et al., "Column-switching techniques in the analysis of phosphate by ion chromatography," *J. Chromatogr. A* 675(1-2):141-147 (Jul. 1994).  
Huang, Y., et al,. "Determination of bromate in drinking water at the low μg/l level by column switching ion chromatography," *J. Liq. Chromatogr. Rel. Technol.* 22(14):2235-2245 (1999).  
Peldszus, S., et al., "Quantitative determination of oxalate and other organic acids in drinking water at low μg/l concentrations," *J. Chromatogr. A* 793(1):198-203 (Jan. 1998).  
Rey, M., et al., "Column switching for difficult cation separations," *J. Chromatogr. A* 789(1-2):149-155 (Nov. 1997).  
Umile, C., et al., "Significant reduction of the detection limit in ion chromatography by relative analyte enrichment with column switching," *J. Chromatogr. A* 723(1):11-17 (Feb. 1996).  
Utzman, S., et al., "Fast analysis of pulping liquors using ion chromatography and column switching," *LC-GC* 9(4):301-302 (Apr. 1991).  
Villaseñor, S., "Matrix elimination in liquid chromatography using heart-cut column switching techniques," *Anal. Chem.* 63(14):1362-1366 (Jul. 1991).

* cited by examiner

*Primary Examiner* — Krishnan S Menon  
*Assistant Examiner* — Rebecca M Fritchman  
(74) *Attorney, Agent, or Firm* — Morgan, Lewis & Bockius LLP; David J. Brezner

(57) ABSTRACT

An ion chromatography apparatus comprising: (a) a first chromatography column, (b) a second chromatography column, the volume of the second column being no greater than 0.9 times the volume of the first; and (c) valving disposed between said first and second columns permitting selective transfer of separated ionic species from first chamber to second chamber for further analysis.

20 Claims, 12 Drawing Sheets

MULTIDIMENSIONAL CHROMATOGRAPHY APPARATUS AND METHOD

BACKGROUND OF THE INVENTION

Trace ions in the presence of matrix ions in environmental samples are commonly analyzed by ion chromatography. Typically, the detection of trace ions is enhanced by pre-concentration or by injecting a large volume of the sample designated as "large loop" injection. In addition to concentrating the species of interest, these approaches also focus or concentrate the matrix ions which may not be desirable in some cases. With the pre-concentration approach, there may be a loss of recovery of trace ions of interest, since a large matrix ion concentration tends to act as an eluent within the concentrator column. In some instances the presence of high levels and varying levels of matrix ions can affect the overall chromatographic performance and can cause higher variances in retention time and peak response reproducibility. In addition, high levels of matrix ions can cause loss of peak efficiency and resolution and decrease in column lifetime. Therefore, there is a need for a reliable ion chromatographic method that allows detection of trace ions in the presence of matrix ions.

Several different approaches have been discussed in the literature to minimize the levels of matrix ions such as pre-treating the sample with a pretreatment column, neutralizing the matrix ions using a neutralizer, and dialysis. The most common approach is to use a column to pre-treat the sample prior to separation to eliminate or to decrease the matrix ion concentration. For example, when the matrix ion consists of chloride, a silver form cation exchanger can be used to precipitate the chloride and thus facilitating the detection of other trace anions in the sample. The above pretreatment or matrix elimination step is either performed inline or offline. The offline steps are cumbersome and time consuming. Inline methods are preferred since they automate the analysis. However, typically the exchanger column is either discarded or reused after regeneration, thus adding to analysis costs and/or additional processing steps. It would be useful to truly automate the analysis.

One way to accomplishing this is by pursuing a two dimensional analysis. Online multidimensional chromatography has been used for analyzing complex samples. In some instances, the approach has been designated as column switching. The approach relies on segmenting the sample analysis chromatogram into manageable portions for further analysis. In the two dimensional approach, the matrix ions could be diverted to waste while the analytes of interest flow to a second column or dimension for further analysis or routed back into the primary column for further analysis. In some cases, the separations were accomplished using a single analytical pump. In some instances, two systems were used for the purpose of analyzing species of interest. The use of a suppressor differentiates two dimensional liquid chromatographic analyses from two dimensional suppressed ion chromatography analysis. The suppressor converts the eluent to the weakly dissociated form. With hydroxide eluents, the suppressed eluent is water which provides a good carrier liquid for concentrating species of interest by focusing onto a concentrator column. The focusing effect of the concentrator column enables analysis without substantial degradation of peak shapes. Although the prior art literature shows multiple columns with multiple chemistries and capacities, there were no means provided for improving the sensitivity of the ions of interest.

The literature describes a number of two dimensional separations. For example, Steven R. Villaseňor (Anal. Chem 63, (1991), 1362-1366 disclosed a matrix elimination technique using heart cut and column switching method for the analysis of sulfite in analgesic formulation. The approach does not use a concentrator column or means for concentrating the heart cut. Additionally a suppressor was not used in this work. The pre-column and the analytical column were operated at a single flow rate.

Umile and Huber (J. of Chromatography, 723, (1996) 11-17) disclose a column switching technique for relative analyte enrichment. The concept is to divert the ions of interest into a second column and obtain improved resolution of peaks of interest. The approach uses a column C1 to run the first part of the separation and cutting the required heart cut into a second column C2. The analysis continues on C2 at the same flow rate to yield higher resolution separations of peaks of interest. This type of approach is not suitable for achieving sensitive detection of ions in the presence of matrix components.

Utzman and Campbell (LC-GC volume 9, 4, 301-302) describe a column switching method to pursue analysis of white liquors and dilute recirculating liquors. The approach uses a guard and an analytical column between which the flow is redirected. Chloride, sulfate and sulfite ions pass through the guard column and then the flow is switched to flow through the analytical column first followed by the guard column. This schematic allowed highly retained thiosulfate ion to elute at a reasonable run time of 9 minutes as opposed to 30 minutes in the standard method without valve switching. The approach uses a fixed flow rate.

Another variation of the above approach is shown by Columbini et. al. (J. Chromatography, A 822, (1998) 162-166) to analyze total nitrogen and phosphorus by switching the column flow with the matrix ions to waste using one pump and pursing the analysis of species of interest using a second pump. An overall reduction in run time along with improved resolution of species of interest was achieved. This approach also used a fixed flow rate.

Galceran and Diez (J. Chromatography, A, 675, (1994) 141-147 show the analysis of phosphate in samples containing high levels of sulfate. The approach used a column switching setup that allowed transfer of analytes of interest from one dimension to another dimension. No suppressors were used in this work. The above approach the two dimensions were operated with the same flow rate.

Rey et. al. (J. Chromatography A, 789 (1997) 149-155) discloses a column switching means for pursuing analysis of cations. The separation of trace inorganic cations in the presence of large concentration of sodium or ammonia was shown. In this approach there is no preconcentration and the divalent cations elute before the monovalent cations. Also a single pump is used in the analysis and the columns are operated at a single flow rate.

Peldszus et. al. (J. Chromatography, A, 793, (1998) 198-203 describes a two step column switching approach. In the first stage, the ion of interest oxalate was focused on to a concentrator column while the other ions are sent to waste. In the second stage the oxalate ion was analyzed using a different gradient method. A single pump was used in the analysis and the columns were operated at a single flow rate.

Huang et. al. (J. Liquid Chromatography, 22, 14, (1999) 2235-2245) shows the analysis of bromate in drinking water. They used a two stage process the first run was a matrix elimination run followed by analysis of bromate. The approach used a concentrator column to concentrate the heart cut after suppressing the eluent similar to the present invention. The analysis however was performed at a single flow rate. In contrast in the present invention the analysis was performed on a second dimension column of a lower volume and operated at the same linear flow rate or overall lower flow rate.

Bruno et. al. (J. Chromatography, A, 1003 (2003) 133-141) shows analysis of inorganic ions in waters of high salinity. The analytes of interest were diverted from the first dimension to the second dimension and then analyzed in the second dimension while the matrix ions were sent to waste in the first dimension. Both dimensions were operated at the same flow rates. In contrast, in the present invention the analysis was performed on a second dimension column of a lower volume and operated at the same linear flow rate or overall lower flow rate.

There is a need for a two dimensional method that provides enhanced sensitivity for ions of interest particularly when they are present along with matrix ions.

SUMMARY OF THE INVENTION

In accordance with one embodiment of the present invention, an ion chromatography apparatus is provided comprising: (a) a first housing defining a first flowthrough chamber containing first separation medium for separating ionic species of one charge, positive or negative, in a liquid sample stream, (b) a second housing defining a second flowthrough chamber containing second separation medium of the same charge as the first separation medium for separating ionic species in a liquid sample stream, the second chamber having a volume no greater than 0.9 times the volume of the first chamber; and (c) first valving disposed between the first chamber and the second chamber permitting selective transfer of ionic species from first chamber to second chamber for further analysis.

Another embodiment is a method comprising (a) flowing an eluent-containing liquid sample stream containing ionic species of one charge, positive or negative, through a first separation medium in a first flowthrough chamber to separate the ionic species, (b) flowing an eluent along with a selected portion of the separated ionic species from the first separation medium through a valve and a second separation medium of the same charge, positive or negative, as the first separation medium in a second flowthrough chamber to further separate the ionic species, the volumetric flow rate through the second separation medium being not more than 0.9 times the volumetric flow rate through the first separation medium, and (c) detecting in a first flowthrough detector the further separated ionic species in the aqueous liquid stream exiting from the second separation medium.

DETAILED DESCRIPTION OF THE PREFERRED EMBODIMENTS

In general, the apparatus of the present invention relates to an ion chromatography method and apparatus which includes two ion separators, typically chromatography columns, for separating ionic species of one charge, positive or negative, in a liquid sample. A valve is disposed between the two separators. Both separators may be of the same type, typically including housings defining flowthrough chambers containing the ionic species separation medium. A guard column may be included along with the separator column. For simplicity of description, the separators will be referred to as columns or chromatography columns which include separation medium, e.g., of a conventional packed bed type or porous monolithic separation medium type.

As will be explained later, the components of the system, e.g., the sample loops and concentration, chromatography columns are not always on line. For example, the valving has positions that permit loading of a concentrator with the sample ions of interest with the effluent from the concentrator in the load position going to waste but not to the second column. Nonetheless, a system with valving that is capable of providing fluid communication, in at least one valving mode, between the chromatography columns will be referred to as valving disposed between the two columns.

A system with two ion separators in series is termed a two dimensional system. The first dimension includes the first chromatography column and any related tubing, and other devices such as a suppressor and detector downstream from the first column but upstream of the second column. The second dimension refers to the second column which is used to perform a second separation of the ions of interest. The second dimension includes a concentrator column, when employed. For suppressed chromatography, the system includes a suppressor downstream from the chromatography column and a detector for detecting the ionic species of interest.

Figure 1:
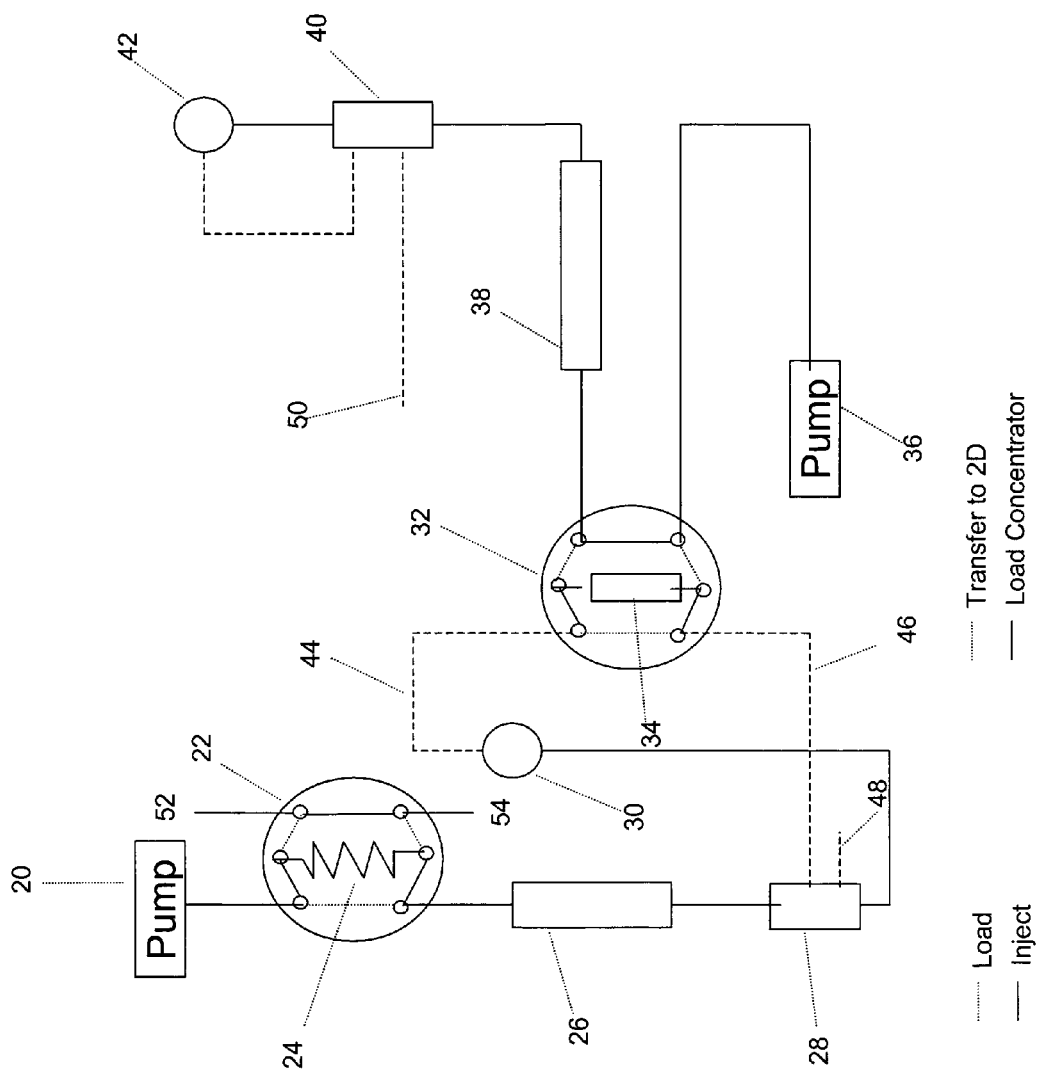
FIGS. 1-4 illustrate schematic views and systems according to the present invention.

FIG. 1 illustrates one embodiment of the present invention. An eluent solution is supplied from a source, not shown, under pressure applied by a pump 20 for flow into the first dimension. The solution flows in a line to injection valve 22 fitted with an injection loop 24. It is preferable that the injection loop have a large volume particularly while pursuing analysis of trace ions. The preferred large injection loop size of the first dimension for a column inner diameter of 4 mm typically varies from about 1 µL to 20 mL, or more preferably from 10 µL-4 mL, or from 100 µL to 2 mL. For a higher or lower inner diameter column, the preferred injection loop size increases or decreases proportional to the column volume.

The sample is suitably injected into loop 24 by an auto sampler 52 (e.g., of the AS40 type supplied by Dionex Corporation) to load the loop 24 in the loop loading position. Sample in excess of the amount required to load the loop is diverted to waste in line 54. During the time that valve 22 is in the loop loading position, the eluent bypasses the loop and flows directly into an analytical column 26. Typically, the analytical column is a chromatography column which includes a housing defining a flowthrough chamber containing ion separation medium for separating ionic species in the eluent stream of one charge, positive or negative. The system will first be described with respect to the separation of anions in which case the separation medium in separator 26 comprises of anion exchange material. The medium can be any ion separation material, such as used in chromatography, e.g., a packed bed of ion exchange resin particles used in a conventional chromatography column, latex agglomerated ion exchange particles, a monolith of ion exchange material with porous flowpaths through the material, or the like.

In a preferred embodiment, suppressor 28 is used in the first dimension, disposed between column 26 and detector 30. This suppressor can be any ion chromatography suppressor so long as it is capable of handling the back pressure from the remainder of the system, and particularly, concentrator column 34, when employed.

In the load operation of the first dimension, the sample solution flows through ion separation column 26 wherein the sample ions are separated and are directed to optional suppressor 28. As illustrated, suppressor 28 is of the membrane suppressor type. In one embodiment, the membrane suppressor is a sandwich membrane suppressor, e.g., as illustrated in U.S. Pat. No. 5,352,360, in which sample solution flows through a central liquid sample flow channel surrounded on both sides by ion exchange membranes which define flanking regenerant flow channels on both sides of the sample flow channel in the suppressor. As in the suppressor of the '360 patent, the solution downstream of detector 30 is recycled through the regenerant flow channel of the suppressor. Any suitable suppressor of the prior art can be used with the present invention.

The effluent from the liquid sample flow channel (not shown) of suppressor 28 flows through detector 30, typically an ion conductivity detector, and from there to valve 32. During loading of loop 24, valve 32 is in a mode in which the liquid exiting from detector 30 bypasses concentrator column 34 and is rerouted back to the regenerant flow channels (not shown) of suppressor 28 and then flows to waste in line 48. The flow bypasses the concentrator column until the valve is switched to concentrate a flow segment comprising the sample ion peak of interest.

After loop 24 is loaded, valve 22 is switched to the inject position. In this position, an eluent solution is pumped by pump 20 through loop 24 to carry the sample into analytical column 26 for the first dimension ionic separation.

The illustrated system is for suppressed chromatography in the first dimension in which the effluent from column 26 flows through suppressor 28 in which the electrolyte of the eluent is suppressed into weakly disassociated form as in conventional in ion chromatography suppressors. The system is also applicable to unsuppressed chromatography in the first or second dimension. The suppressed effluent of the sample flow channel of suppressor 28 then flows to detector 30 which detects the ionic species of interest. For ion conductivity detector or other detector of choice, the detection results in ion chromatograph. Detection by optional detector 30 serves the function of identifying the segment of interest and can be used to divert the segment of interest into the next dimension.

During the loading of sample in loop 24, valve 32 is preferably in the inject position and the concentrator column 34 is bypassed from the effluent flow from detector 30 and the effluent flow from detector 30 flows out of valve 32 and is routed to suppressor 28 to serve as the regenerant solution. During the injection step, the suppressed eluent stream from detector 30 is routed through concentrator column 34 to focus the ions of interest. The effluent flowing out of concentrator column 34 is routed back to the suppressor 28 to serve as the regenerant solution. An optional gas removal device, not shown, (e.g., of the type sold by Dionex Corporation under the CRD mark and as disclosed in U.S. patent application Ser. No. 10/924,236, filed Aug. 23, 2004) may be placed between cell 30 and concentrator column 34 to remove gases such as carbon dioxide from the suppressed eluent stream prior to the focusing step.

When valve 32 is switched to the injection position, eluent under pressure from the second dimensional pump 36 is routed through concentrator column 34 to elute the species of interest in a flowing eluent solution which flows to a second analytical (chromatography) column 38 in which the second stage of separation is performed. For suppressed ion chromatography, the effluent of the separated ions of interest flow in the eluent to suppressor 40 in which the eluent is suppressed and the ions of interest are detected by detector cell 42 which may be of the same type as detector 30. In this instance, the suppressor may be a membrane suppressor of the same type as suppressor 28. The cell effluent may be routed back to suppressor 42 into the regenerant flow channels as a regenerant stream and routed to waste in line 50. Any suppressor of the prior art can be used in place of suppressor 28.

In one aspect of the present invention, the sample ions are analyzed along with matrix ions (of the same charge as the sample ions) in the first dimension at a flow rate suitable for the first dimension separation column 26. For example, in one embodiment, the separated column is a standard bore chromatography column having a 4 mm internal diameter. However, columns of other sizes and shapes may be employed. For example, the column 26 may be a capillary column (e.g., of id 0.01 mm to 0.1 mm) or other diameters such as 0.01 mm to 10 mm. The absolute size of the columns 26 and 38 can vary. However, one aspect of the invention relates to a reduction in the volumetric flow rate, cross-sectional area perpendicular to flow, and/or volume of the second column relative to the first column.

In the second dimension, the analytes separated in the first dimension are selectively concentrated and retained in concentrator column 34. Column 34 may be of a conventional type such as sold by Dionex Corporation under the trademark TAC-LP1, including a packed bed of ion exchange particles.

The function of an ionic species concentrator column is to concentrate ions. In contrast, the chromatographic column is primarily designed to resolve ionic species. In the process of resolving species, the chromatographic column dilutes the sample zones. In this regard, the chromatographic column is a diluter in contrast to a concentrator column that servers the purpose of focusing analytes. In operation, the concentrator column focuses the ions of interest in one direction and the ions of interest are eluted off the column in the reverse direction to ensure a sharp unresolved focused sample slug. The unresolved sample zone is then diverted into the chromatographic column for further separation. Since the elution step is preferably in the reverse direction to the concentrating step the volume of the concentrator column is not critical as long as the concentrator has adequate capacity to concentrate species of interest. Typically, the concentrator column capacity varies from 1 ueqv/column to about 30 ueqv/column. Higher concentration of sample ions demanding higher capacity concentrator columns. The backpressure of the concentrator column may be optimized as a function of the pressure requirements of the sample dispensing device such as an autosampler. Lower backpressure concentrators are preferred when dispensing sample at high flow rates from pressure sensitive sample dispensing pumps or auto sampler pumps.

The concentrator column comprises a medium that can be any ion separation material, such as used in chromatography, e.g., a packed bed of ion exchange resin particles used in a conventional chromatography column, latex agglomerated ion exchange particles on the exterior of core ion exchange resin particles, a monolith of ion exchange material with porous flowpaths through the material, or the like.

The focused analytes of interest are eluted off concentrator column 34 by the eluent from pump 36 and analyzed using the second dimensional separator column 38, typically of the same general type as separation column 26.

Concentrator column 34 serves to preconcentrate the sample ions of interest for analysis in the second dimension. Column should have adequate capacity to concentrate the species of interest and/or exhibit higher selectivity for the ions of interest in comparison to the matrix ions. A rinse step can be incorporated into the analysis system during the preconcentration step to facilitate further matrix ion removal and allow for quantitative analysis of the analytes of interest.

In one embodiment, the second dimensional separator column 38 includes a chamber, retaining separation medium, of lower cross-section and/or volume than the primary column. For a column with circular dimensions, a lower cross sectional area implies a column with a lower internal diameter which in turn also implies that the column volume is lower. For a second column with a similar column id. the volume can be lower if the column length is shorter than the first column. In a specific embodiment, the second separator is operated at the same linear velocity (L)(cm)/t(min) as the primary column 36. This embodiment permits enhanced detection of species of interest and improved sensitivities of peaks of interest with concentration sensitive detectors. In the case when the column cross section is low, in order to operate at the same linear velocity as the primary column, the second column has to be operated at a lower flow rate. A lower flow rate implies lower dilution of the separated analytes. Additionally the peak response increases since the analyte peak is traveling through the detector cell at a low flow rate. Hence higher sensitivity is observed when using lower flow rates with concentration sensitive detectors such as conductivity or UV detectors. Since the mass of the analyte is unchanged, mass sensitive detectors show minimal change in sensitivity.

In one embodiment, the volumetric flow rate through the second column is no greater than 90% of the flow rate through the first column, and preferably no greater than 80%, 70%, 60%, 50%, 40%, or less.

In another embodiment, the chamber of the second column has a volume no greater than 90% of the first column chamber, preferably no grater than 80%, 70%, 60%, 50%, 40%, or less. As defined herein, the chamber is the portion of the chamber defining the separation medium. If full, they are substantially the same; but if the chamber is partially full, then the chamber volume comprises that part of the chamber in contact with the medium.

In a further embodiment, the cross-sectional area of the second chamber is no greater than 90% of the first chamber, preferably no greater than 80%, 70%, 60%, 50%, 40%, or less.

Another advantage of the present two dimensional approach is that the injection volume in the first dimension can be increased without significantly impacting the chromatographic performance of the second dimension separation. This may be because the first dimension is used to divert the matrix while the second dimension is used to selectively concentrate and separate the analytes without the interference from the matrix ions.

Columns 26 and 38 can have a conventional circular cross-section defining the cross-section of the separation medium. However, other geometric shapes could be employed. For example, the separation medium could be defined in the form of relatively rectangular chambers or channels transverse to flow.

As set forth above, one aspect of the invention is to reduce the volumetric flow rate through the ion exchange medium and separator 38 compared to that of separator 26. This permits enhanced detection of the ionic species of interest and improves the sensitivity of peaks of interest using concentration sensitive detectors. An advantage of this approach is that the injection volume in the first dimension can be increased without significantly impacting the chromatographic performance in the second dimension.

One way to accomplish the same linear velocity (L)(cm)/t(min) in the second separation medium compared to the first separation medium is to reduce the internal cross-sectional area and/or volume of the second separation column relative to the first column while maintaining a reduced flow rate. As an approximation of the cross-section and volume of separation medium, the cross-section of the column perpendicular to flow and the volume of interior of the column in which the medium is disposed may be used. To control the reduction in volumetric flow by reduction in the transverse cross-sectional area, it is preferable that the second column have an inner cross-sectional area no greater than 0.9 times, preferably no greater than 0.8 times, and more preferably no greater than 0.5 times that of the first column. For example, for a 4×250 mm column in the first dimension operated at 1 ml/min flow rate, the second dimension may be operated at 0.25 ml/min using a 2×250 column. This combination maintains the linear velocity while resulting in an expected four-fold sensitivity enhancement for the second dimension over the first dimension. The system provides means for minimizing the matrix components as well as providing improved detection sensitivity for the ions of interest.

For a cylindrical column, the internal diameter of the first column suitably is about 0.01 mm to 10 mm regime, more preferably 1 mm to 9 mm regime, and most preferably 2 mm to 4 mm regime. In one embodiment, the second dimension is of the same length as the first dimension but with a lower internal diameter. In this approach, the preferred internal diameter for the second dimension is 0.01 mm to 9 mm, more preferably 0.025 mm to 2 mm, and most preferably 0.5 mm to 2 mm.

The above approach assumes similar linear velocities through the first and second columns. However, by using separate pumps for liquids in the two columns, the volumetric flow rate in the second column may be reduced relative to that of the first column without altering the respective dimensions of the first and second columns. Further, a combination of changes in the parameters of relative column dimensions and linear flow rates may be employed to accomplish the desired enhancement detection and improved sensitivity of peaks of interest. It is also possible to split the flow in the first dimension and divert the split flow into the second dimension separator.

In the first dimension separator column 26, it is preferable to use separation medium of relatively high capacity to permit separation and removal of high ionic strength matrix ion of the same charge as the analyte ions which can be separated and removed prior to separation in the second dimension. For example, for a separation column with an inner diameter of 4 mm, a suitable capacity range is from 1-1,000 μeqv/column, preferably 100-400 μeqv/column, and most preferably about 150-350 μeqv/column. The capacity is related to the anticipated concentration of matrix ion which could otherwise interfere with analysis of the analyte ions of interest. The capacity can be adjusted by using high capacity separation medium or by adjusting the volume of the column, or both.

It is preferred to use column chemistries that preferentially retain the analytes of interest over the matrix ions. For example, while pursuing perchlorate analysis a Dionex Corporation AS16 column is used since for separation this phase shows a higher selectivity for perchlorate over the matrix ions. If the matrix ion concentration exceeds the column capacity, then a sample pretreatment to reduce the matrix ions may be used. Referring to the preconcentrator column, it should have adequate capacity to concentrate the species of interest and/or exhibit higher selectivity for the analytes of interest. Any additional rinse steps can be incorporated to the concentration step to facilitate further removal of matrix ions and maintain the retention of analytes of interest and facilitate quantitative analysis.

In another embodiment of the first dimension (not shown), a large loop is employed in place of concentrated column 34 in the transition to the second dimension. The large loop facilitates selective transfer of ions of interest into the second dimension. The loop would hold the sample zone of interest and transfer this to the second dimension. In this embodiment, a sample loop, e.g., of the same type as loop 24, may be employed in place of concentrator column 34.

Optionally, a pre-concentrated column, not shown, (e.g., of the same type as concentrator 34) may be used in place of the sample injection loop and prior to column 26 in the first dimension so long as the column has adequate capacity to concentrate the ionic species of interest and/or exhibits higher selectivity for the analytes of interest than the matrix ions. Any additional rinse steps can be incorporated into the pre-concentration step to facilitate further removal of matrix ions and maintain the retention of ions of interest and facilitate quantitative analysis.

As set forth above, valve 32 is disposed between the first and second dimensions. The first and second dimensions are not always in fluid communication as various steps are employed in isolation in each of the two dimensions. However, as used herein, the disposition of a valve between the two columns means that at some time in the analysis cycle valve 32 has a setting in which sample flows from the first dimension to the second dimension, preferably by use of a concentrator device also disposed between the two dimensions.

A wide variety of valves including standard chromatography valves that would permit sample injection in the first dimension and enable cutting volume segments from the first dimension separation stream and enabling transfer to the second dimension would be suitable for the present invention. Preferable valves include 6. and 10 port configurations such as sold by Dionex Corporation. The liquid contact portions of the valves are preferably made of PEEK.

In a preferred embodiment, concentrator column 34, controlled by a valve 32, is disposed between the first and second dimensions. The sample is loaded in the first dimension and a cut volume is transferred to the second dimension. As used herein, the term "cut volume" means the volume diverted from column 26 in the first dimension to concentrator column 34 and ultimately to the second dimension for further analysis. A preferred cut volume may be expressed in terms of the time for a given application flow rate. Suitably, the cut volume varies from 0.01-20 minutes, or more preferably, 0.2-5 minutes, and most preferably about 2-4 minutes. The cut volume is chosen for a given target analyte and is optimized for the analyte in the presence of matrix ions of varying concentrations. It is preferable to use a smaller cut volume since a larger cut volume may divert a larger portion of the matrix ions into the second dimension. The cut volume can be derived by running a standard in the presence and absence of the highest concentration of matrix ions and optimize the cut time window to achieve the maximum peak response recovery for the peak of interest.

For suppressed ion chromatography, a suppressor 40 is used in the second dimension. As illustrated, the suppressor 40 may be of the same membrane suppressor type as suppressor 28 in which effluent from detector 42 is used as the regenerant solution in the regenerant flow channel of the suppressor. Suppressor 40 is not constrained by the back pressure limitations to accommodate concentrator column 34.

More than one cut volume segment can be diverted for analysis in the second dimension or even further dimensions. By using appropriate valving schemes the concentrator column could be used to selectively capture all peaks of interest while diverting the matrix ions to waste. It is also possible to use a third dimension by using a second valve and a third separator column with similar reduced dimensions to that of the second column and using a third suppressor and detector. For analysis in more than two dimensions, the columns in the third or more dimensions preferably have lower volumetric flow rates than the first dimension and are preferably operated at the same linear flow rate as the first dimension.

The conduits used for the ion chromatography connection are dependent on the dimensions of the column. For example, 0.01 inch id tubing typically is used for 4 to 9 mm column applications. Similarly, 0.005 inch tubing is used for 3 mm columns and 0.003 inch id for 1 mm internal id columns. Lower id tubings are preferred for lower id columns as large bore tubing can result in larger band dispersion. Higher band dispersion may offset the expected sensitivity gain hence it is preferable to scale down the dimensions of the connecting tubing when scaling down the secondary column dimensions and flow rate.

As set forth above, it is preferred to operate the two columns at the same linear flow rate so long as the conduits and other chromatographic components are scaled down proportionally to minimize the delay volume for a particular separation. Using the same linear flow rate has the advantage of providing higher sensitivity due to lower dilution of the species of interest and higher response from concentration sensitive detectors.

The preferred operational flow rate ratio, designated herein as F, between the flow rate of the first dimension and that of the second dimension has a wide range, e.g., could be in excess of 1 to 200,000 or more. The sensitivity enhancement is approximately proportional to the F ratio. Excellent sensitivity enhancement can be realized for the species of interest by eliminating or minimizing the matrix ion or matrix ion effects by diverting collectively the species of interest with minimal amount of matrix ions from the first dimension to the second dimension. By optimizing the cut volume for a given application excellent recovery could be realized. For example, if the first dimension column is a 4 mm id column operated at 1 ml/min and the second dimension is a 1 mm id column operated at 0.05 ml/min, then the sensitivity improvement would be on the order of 20 times and is defined by the operational flow rate ratio. This level of sensitivity would enable detection of ultra trace components in the presence of matrix ions.

The concentration of matrix ions can vary over a wide range depending on the sample source. Thus, matrix ions may have a concentration from as little as 5 to 10 times to as high as $10^{12}$ times the analyte concentration. For example, some well water samples can have matrix ions in at a concentration of $10^6 \times$ the level of analyte ions.

Detectors 30 and 42 may be of any conventional type. For example, sensitivity enhancement can be observed for concentration sensitive detectors such as those of the conductivity, amperometry UV, fluorescence, spectrometry or other types. A post-column derivatization reaction can be performed on the analytes of interest after the second dimension separation to facilitate detection of the analytes of interest.

Figure 2:
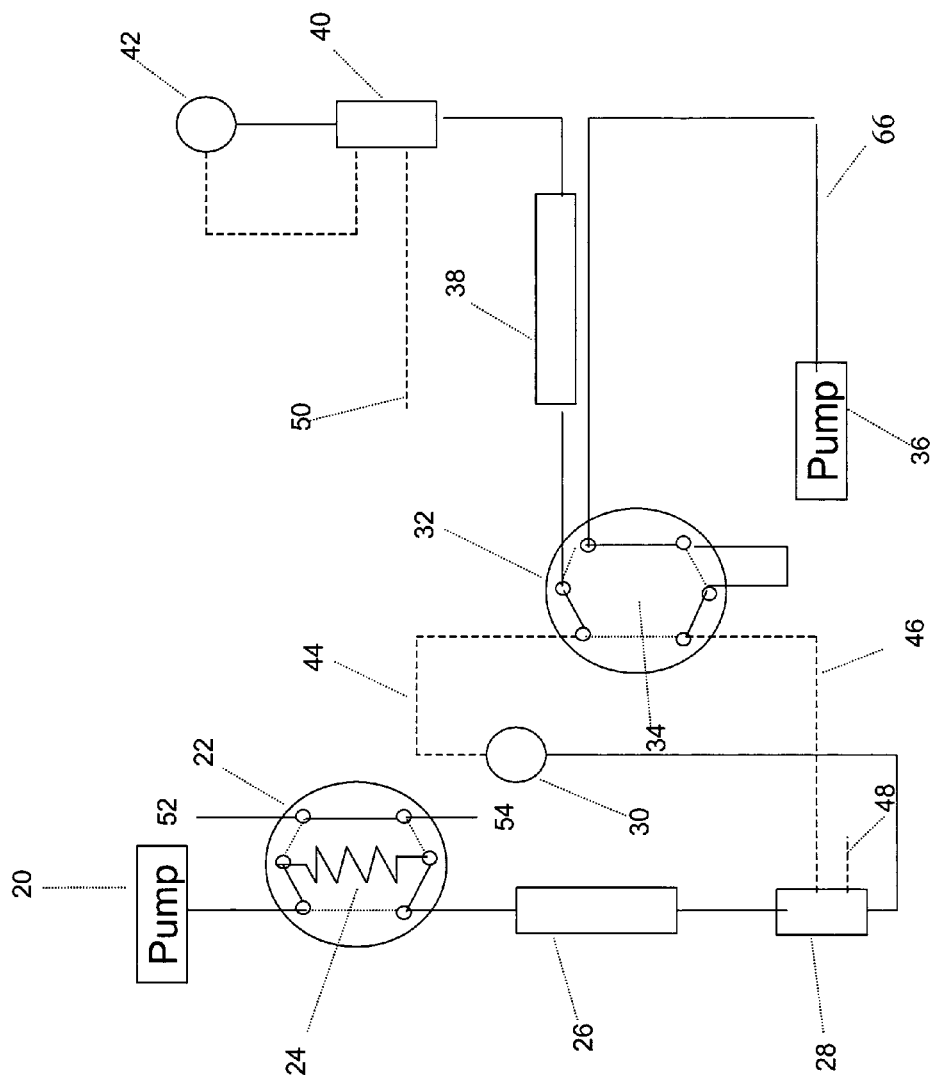

In another embodiment (not shown), the cut volume of interest from the first dimension is diverted directly to the second dimension as shown in FIG. 2. In this embodiment, the concentrator column is not used and the valve 32 is used to divert the cut volume into the second separator column 38.

The sample is loaded as before and separated in column 26. During the load stage of the diverter valve 32, the cut volume or segment of interest is diverted into the second dimension column 38 and during this time the flow from the pump 36 is diverted as regenerant flow into suppressor 28. In the inject stage of the diverter valve 32, the flow from pump 36 is redirected to the column 38 and separation is effected as before without the interference from matrix ions. As in the illustrated embodiment, the second dimension has a lower volumetric flow rate than the first dimension and preferably operates with the same linear flow rate and as per the present invention this setup results in enhanced sensitivity. In this embodiment, when a suppressor is used in the first dimension it should be capable of handling the backpressure from the second dimension. The suppressor can be eliminated in the first or second dimensions.

Figure 3:
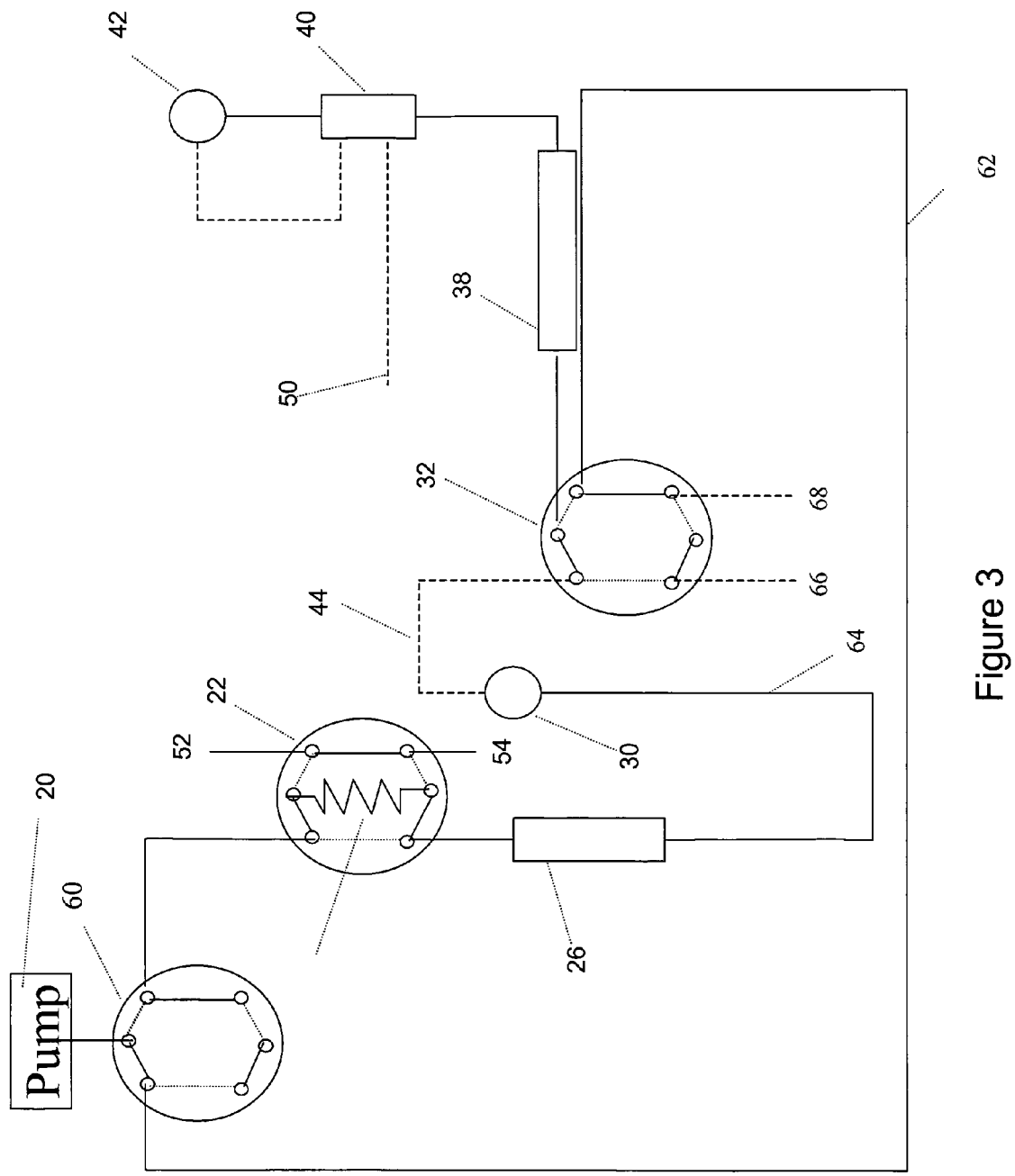

In another embodiment shown in FIG. 3, the present invention could be implemented using a single system consisting of a single pump and a column switching valve to switch between the first and second dimensions. This setup uses only one pump 20. The flow from the pump can be directed to the first dimension column 26 or the second dimension column 38 via switching valve 60 by switching the valve position. In this setup, the sample is injected using valve 22 as discussed above, and separation is effected in column 26. The cut volume of interest is diverted into column 38. The sample that is retained in column 38 is then analyzed by running the pump 20 at a lower volumetric flow rate than the first dimension separation and preferably operated with the same linear flow rate. This setup of the present invention results in enhanced sensitivity for the peaks of interest. It should be noted that the above could also be implemented by manually replumbing the system and directing the flow between the two dimensions.

In another embodiment, when carbonate or biscarbonate eluents are used, residual background originating from the suppressed eluent in the cut volume may be removed prior to the concentration step. Residual carbonic acid after suppression is weakly disassociated and can elute the species of interest off the concentrator column. Removal of carbon dioxide may be accomplished by a device including a gas permeable membrane such as sold by Dionex Corporation under the trademark CRD.

Carbonic acid is weakly dissociated to bicarbonate anion and at high concentration during preconcentration can act as an eluent leading to poor recovery of analytes of interest. By placing the CRD device before the concentrator column, removal of $CO_2$ from the cut volume is accomplished, and this results in the analytes being concentrated in predominantly water background. In other applications with hydroxide eluents presence of a large level of $CO_2$ may interfere with the preconcentration step or the second dimension separation step. Under these conditions a CRD like device may be needed. A CRD like device in the present embodiment would also be useful for removing other volatile species such as ammonia.

Figure 4:
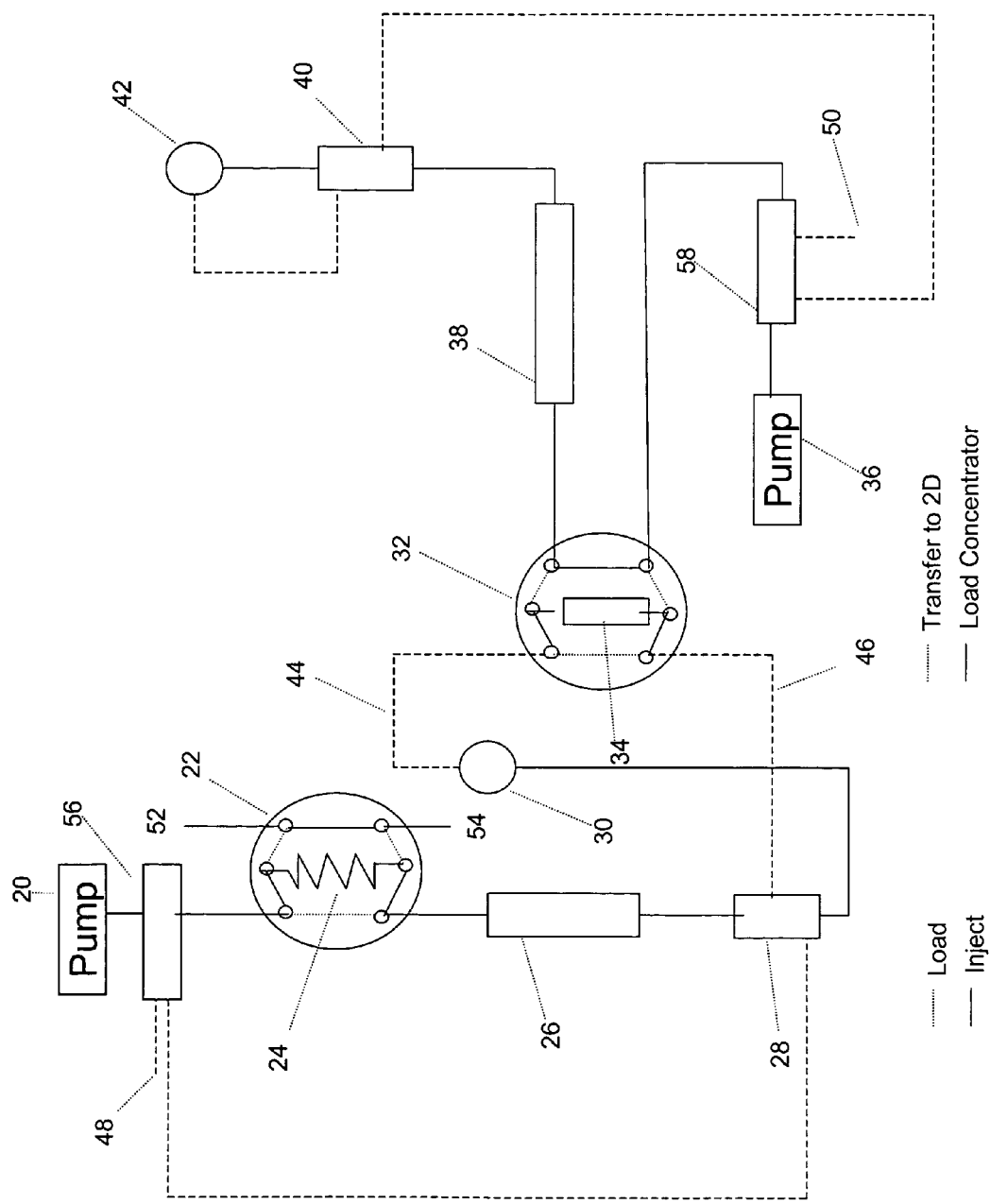

Referring to FIG. 4, another embodiment of the two dimensional invention of the present invention is illustrated which employs eluent generator modules 56 and 58 (not shown) such as of the type illustrated in U.S. Pat. No. 6,225,129 and sold by Dionex Corporation. Like parts will be designated with like numbers for the embodiments of FIGS. 1 and 4. Pumps 20 and 36 are used to pump water, preferably deionized water, through eluent generator modules 56 and 58 includes eluent generation cartridges (not shown), and a continuously regenerated trap column (sold under the trademark CRTC) to purify the eluent. The purified eluent from modules 56 and 58 may be routed through a degasification module (not shown) such as of the type described above to remove electrolytic gases. The eluent exits the eluent generation cartridge 56 and is routed through injection valves 22 and 32, respectively, as illustrated in FIG. 2. The rest of the plumbing and description of individual components are similar to those described with respect to FIG. 1 except that the suppressor waste from suppressor 40 is routed back to eluent generator module 58 to provide water for the regeneration stream flowing through the gas removal device and eluent generator degas modules (not shown). The waste stream is then routed to waste through lines 48 and 50.

In operation of the preferred embodiments of FIGS. 1 and 4 in which a concentrator column is employed, analytes of interest are diverted into concentrator column 32 from the first dimension. The second dimension column has lower volume and is operated at preferably the same linear flow rate as the first dimension column.

The systems of FIGS. 1 and 4 illustrate a recycle mode of operation. However, if desired, an external water mode of operation may be used in which water from an external source is used as the regenerant stream of the suppressor and gas removal devices.

The following examples illustrate different non-limiting examples showing details of the present invention.

Example 1

This example illustrates the limitation of prior art methodology for bromate analysis in the presence of matrix ions. A commercially available Ion chromatograph system ICS 3000 from Dionex Corporation was used for this work. The first dimension column was a 4 mm AG19/AS19 column that was operated using a KOH gradient at 30 C as outlined below.

| Time | Gradient (mM) |
|---|---|
| 0 | 10 |
| 10 | 10 |
| 25 | 45 |
| 30 | 45 |
| 30.1 | 10 |
| 35 | 10 |
| Matrix Concentration (ppm of Cl and SO4) | |
| A | 0 |
| B | 50 |
| C | 100 |
| D | 150 |
| E | 200 |
| F | 250 |

Figure 5:
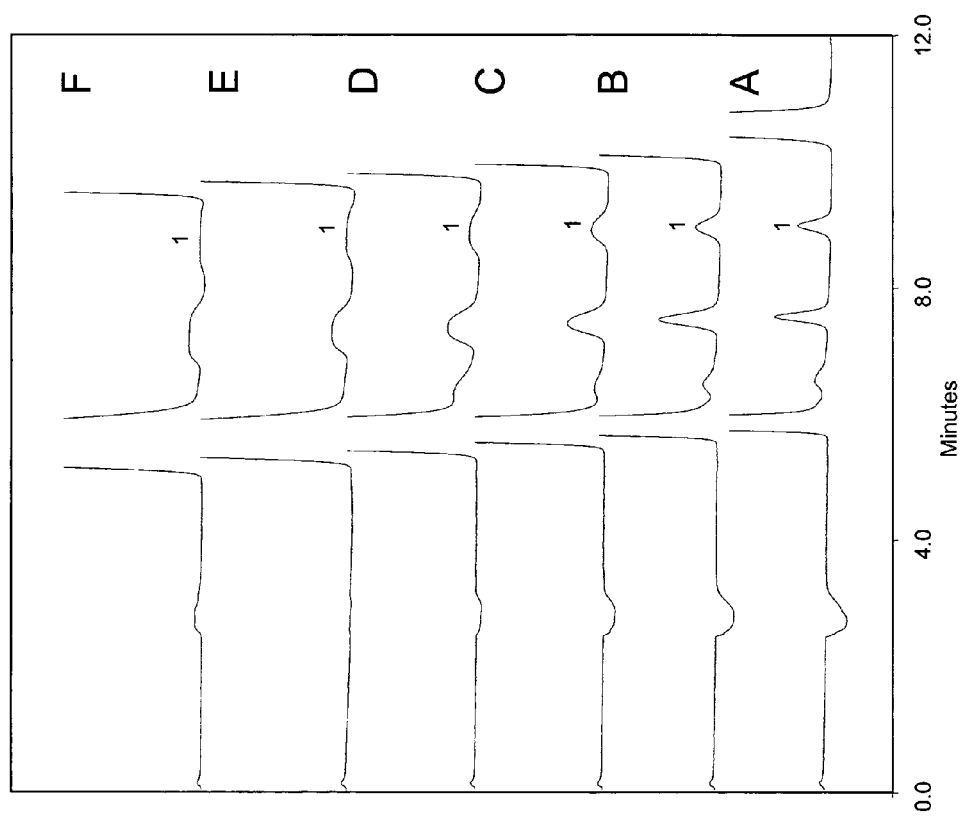
FIGS. 5, 6, 8 and 10 illustrate chromatograms using prior art methods.

A 4 mm ASRS Ultra II suppressor was used for this work and was operated using a constant current of 113 mA. A 500 uL injection loop was used for this work. The effect of matrix concentration (NaCl and Na2SO4) on the bromate peak was studied using the first dimension setup. FIG. 5 shows an overlay of the chromatograms generated using the various matrix samples. The peak labeled 1 is a 5 ppb sample of bromate. It is clear that as the matrix concentration increased from 0 to 250 ppm, the bromate peak became wider and it was difficult to integrate the peak.

Figure 6:
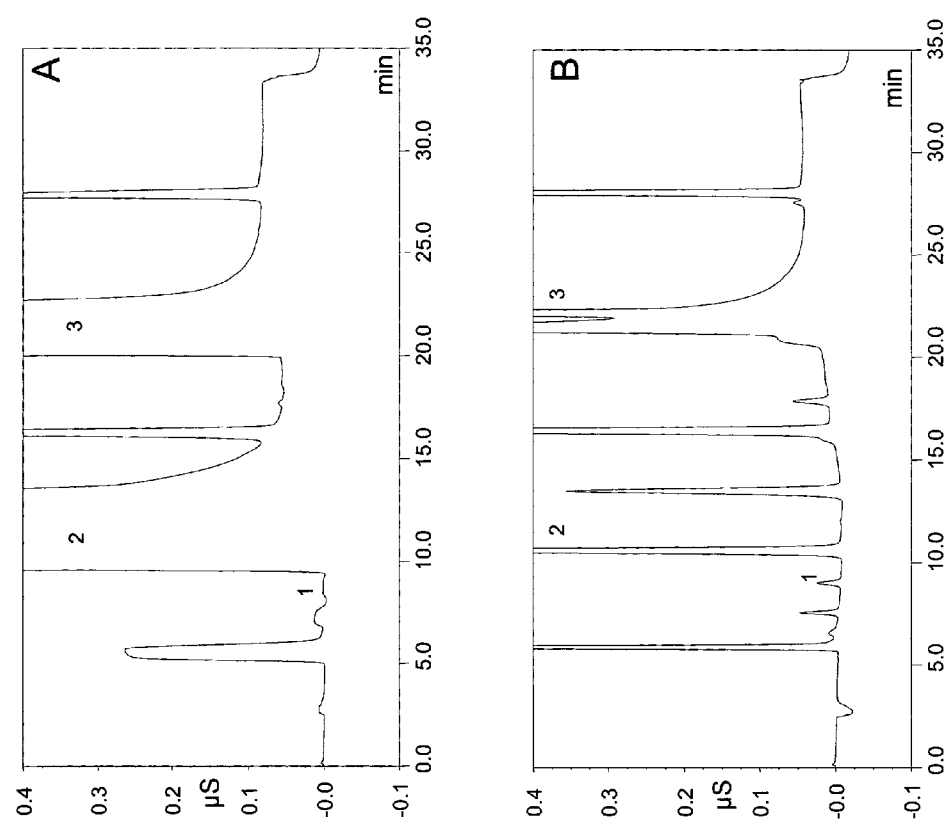

FIG. 6 shows an example of 5 ppb bromate along with a 1000× dilution of a 7 anion standard P/N 56933 from Dionex Corporation using the conditions listed in example 1 with no added additional matrix ions (Inset B) and with additional 250 ppm of chloride (peak 2) and sulfate (peak 3) ions (insert A). The results once again show that as the matrix concentration increased, the ability to integrate and quantitate bromate became difficult.

Example 2

In this example, the bromate sample was analyzed as per the present invention. The first dimension separation conditions were similar to what was outlined in Example 1.

A cut volume from about 7.5 to 9.5 minutes (2 mls) was diverted from the first dimension into a TAC-ULP1 concentrator column and the retained ions were analyzed in the second dimension using a 2 mm AG19 and AS19 column operated at 0.25 ml/min using a KOH gradient at 30 C as outlined

| First dimension Time (min) | Second dimension Gradient (mM) | Gradient (mM) |
| --- | --- | --- |
| 0 | 10 | 10 |
| 10 | 10 | |
| 19.5 | | 10 |
| 25 | 45 | |
| 30 | 45 | |
| 30.1 | 10 | |
| 34.5 | | 45 |
| 35 | 10 | 45 |

Figure 7:
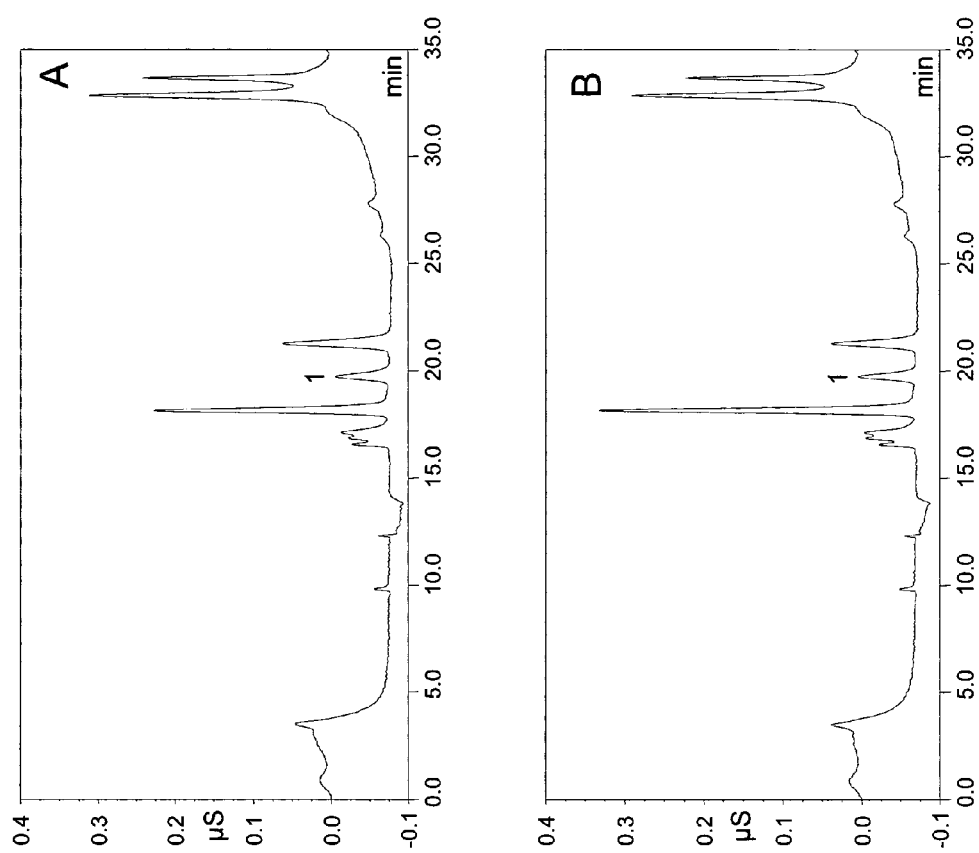
FIGS. 7, 9, 11 and 12 are chromatograms illustrating use of the present invention.

A 2 mm ASRS Ultra II suppressor was used at 29 mA. The same bromate sample (5 ppb of bromate) from FIG. 6 was used in this work. The results indicated excellent recovery of bromate in the presence of matrix ions with no impact on peak shape as shown in FIG. 7 (Inset A is in the presence of additional matrix ions and B is in DI water).

Example 3

The following table compares the peak response of 5 ppb bromate in reagent water in the first dimension versus the second dimension approach of the present invention.

| Dimension | Peak response (peak area) | Sensitivity | Flow rate |
| --- | --- | --- | --- |
| First | 0.0063 | 1 | 1 ml/min |
| Second | 0.0244 | 3.87 | 0.25 ml/min |

It should be noted that the sensitivity in the above example increased roughly four fold as predicted by theory and was proportional to F the ratio of the flow rate the first dimension to the second dimension.

Example 4

The effect of the matrix concentration on bromate recovery was studied in this example using the conditions listed in Example 2 as per the present invention.

The recovery of 5 ppb of bromate ion for a variety of matrix concentration (from 0 ppm to 250 ppm of chloride and sulfate) are shown below.

| Matrix Concentration (ppm) | Bromate Peak Area | Recovery |
| --- | --- | --- |
| 0 | 0.0248 | 100% |
| 50 | 0.0245 | 98.8% |
| 100 | 0.0250 | 100.8% |
| 150 | 0.0244 | 98.4% |
| 200 | 0.0249 | 100.4% |
| 250 | 0.0249 | 100.4% |

It is clear from the above results that the method of the present invention yields excellent recoveries under a variety of matrix concentrations. Consistent sensitivity enhancement is observed for the above samples.

Example 5

Figure 8:
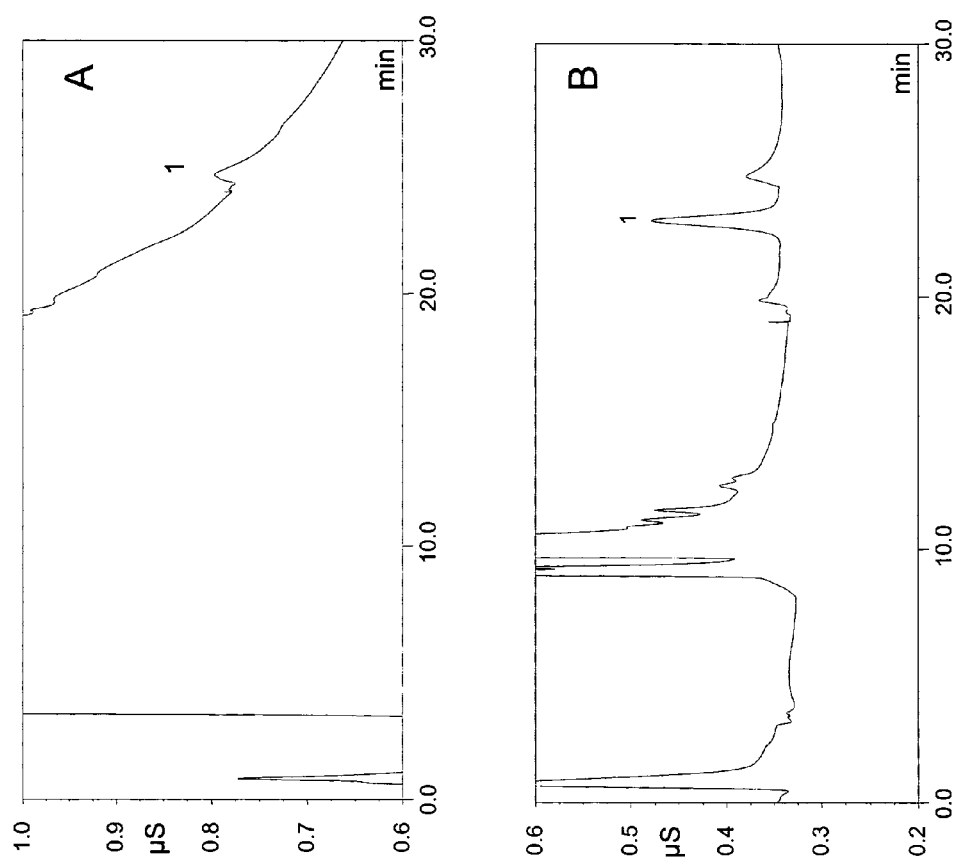

In this example, a first dimension analysis of 5 ppb of perchlorate in the absence of matrix ions and in the presence of matrix ions comprising of 1000 ppm of chloride, bicarbonate and sulfate ions was done using a large loop (4 ml injection) and AG20 and AS20 chemistry. The eluent was 35 mM KOH at 1 ml/min. An ASRS Ultra II 4 mm suppressor was used here at a set current of 87 mA. The results (FIG. 8) indicated poor recovery and peak shape of perchlorate in the presence of the matrix (Inset A peak labeled 1) using the direct injection of a large sample volume. Inset B shows the perchlorate peak (peak labeled 1) when it was analyzed without the added matrix ions.

Example 6

Figure 9:
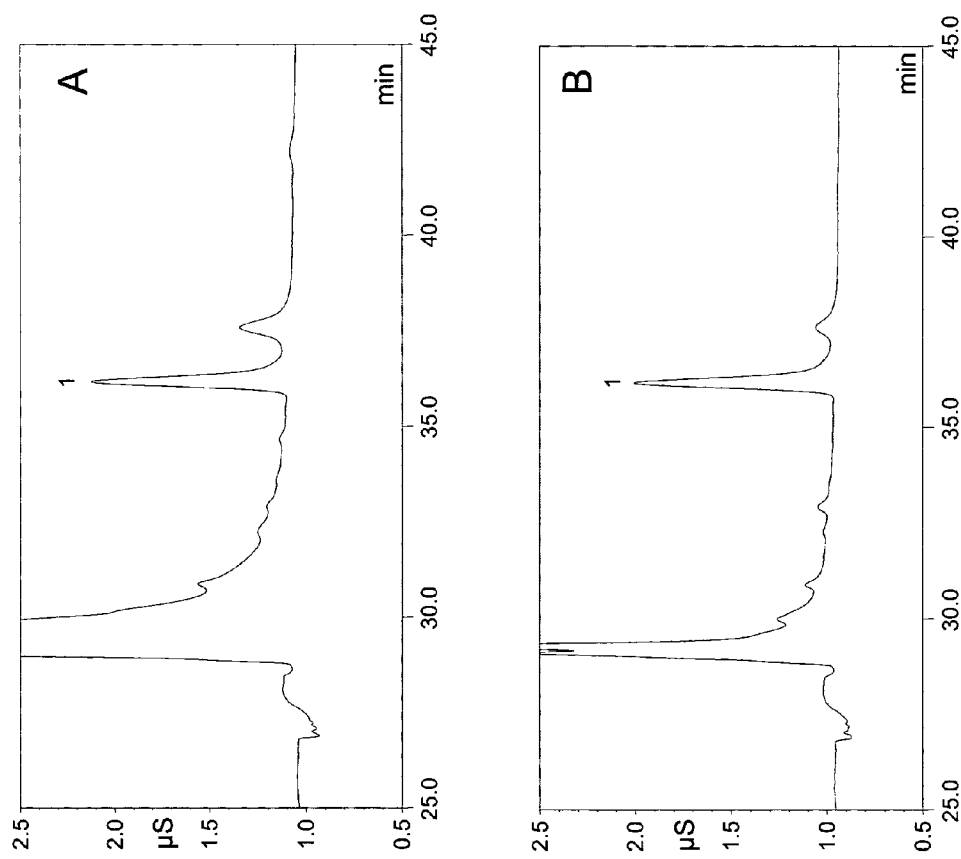

In this example, a two dimensional analysis as per the present invention of 5 ppb perchlorate is shown using the samples from example 5. The first dimension conditions were similar to what was described in example 5. A cut volume from 19 to 24 minutes (5 ml) was diverted as per the present invention into a TAC-ULP1 concentrator column and subsequently analyzed in the second dimension. The second dimension analysis was done using a 2 mm AG20/AS20 column operated at 0.25 ml/min using an eluent comprising of 60 mM KOH. An ASRS Ultra II 2 mm suppressor was used in the second dimension and operated at a current setting of 38 mA. The results as shown in FIG. 9 indicated excellent recovery of perchlorate (Inset A peak labeled 1) in the presence of matrix ions. The prechlorate response was roughly similar with (Inset A) and without (Inset B) the matrix. The peak shape was also maintained as shown in FIG. 9. These results indicate excellent utility of the present method for perchlorate analysis.

Example 7

The following table compares the peak response of 5 ppb perchlorate in reagent water in the first dimension versus the second dimension approach of the present invention.

| Dimension | Peak response (peak area) | Sensitivity | Flow rate |
| --- | --- | --- | --- |
| First | 0.072 | 1 | 1 ml/min |
| Second | 0.352 | 4.88 | 0.25 ml/min |

The above results demonstrate the improved sensitivity of the present invention versus the first dimension approach.

Example 8

The following table shows the recovery of 5 ppb of perchlorate under a variety of matrix (chloride, sulfate and bicarbonate) concentrations. Excellent recovery of peak response is observed by the present invention. This level of recovery is not possible with the first dimension approach under large loop conditions. These results also demonstrate consistent sensitivity improvement as per the present invention. Additionally as per the present method it is possible to inject large volumes in the first dimension without impacting the peak shapes in the second

| Matrix Concentration (ppm) | Perchlorate Peak Area | Recovery |
|---|---|---|
| 0 | 0.3522 | 100% |
| 50 | 0.3560 | 101.1% |
| 100 | 0.3567 | 101.3% |
| 200 | 0.3509 | 99.6% |
| 500 | 0.3505 | 99.5% |
| 800 | 0.3468 | 98.5% |
| 1000 | 0.3438 | 97.6% |

Example 9

Figure 10:
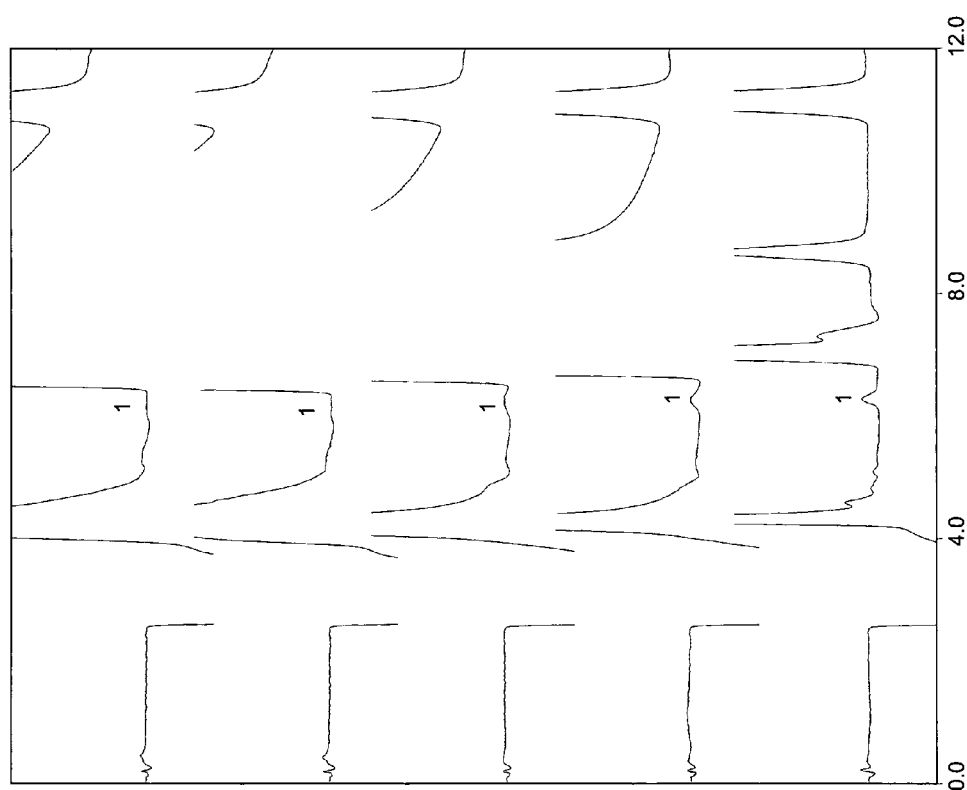

This example shows the analysis of 5 ppb of bromate under a variety of matrix concentrations (Chloride and sulfate) from 0 ppm to 200 ppm using the present methodology for analyzing Bromate. An AS9HC column was used in this work using 9 mM sodium carbonate eluent along with a 4 mm AAES suppressor and conductivity detection. It is clear from the results shown in FIG. 10 that the bromate (peak labeled 1) peak width increases with increasing matrix concentration to the point that peak recovery suffers significantly. Although this example shows conductivity detection it is clear that the presence of matrix ions will impact the peak shapes using post column derivatization and UV detection.

| Matrix Concentration (ppm of Cl and SO4) | |
|---|---|
| A | 0 |
| B | 50 |
| C | 100 |
| D | 150 |
| E | 200 |

Example 10

Figure 11:
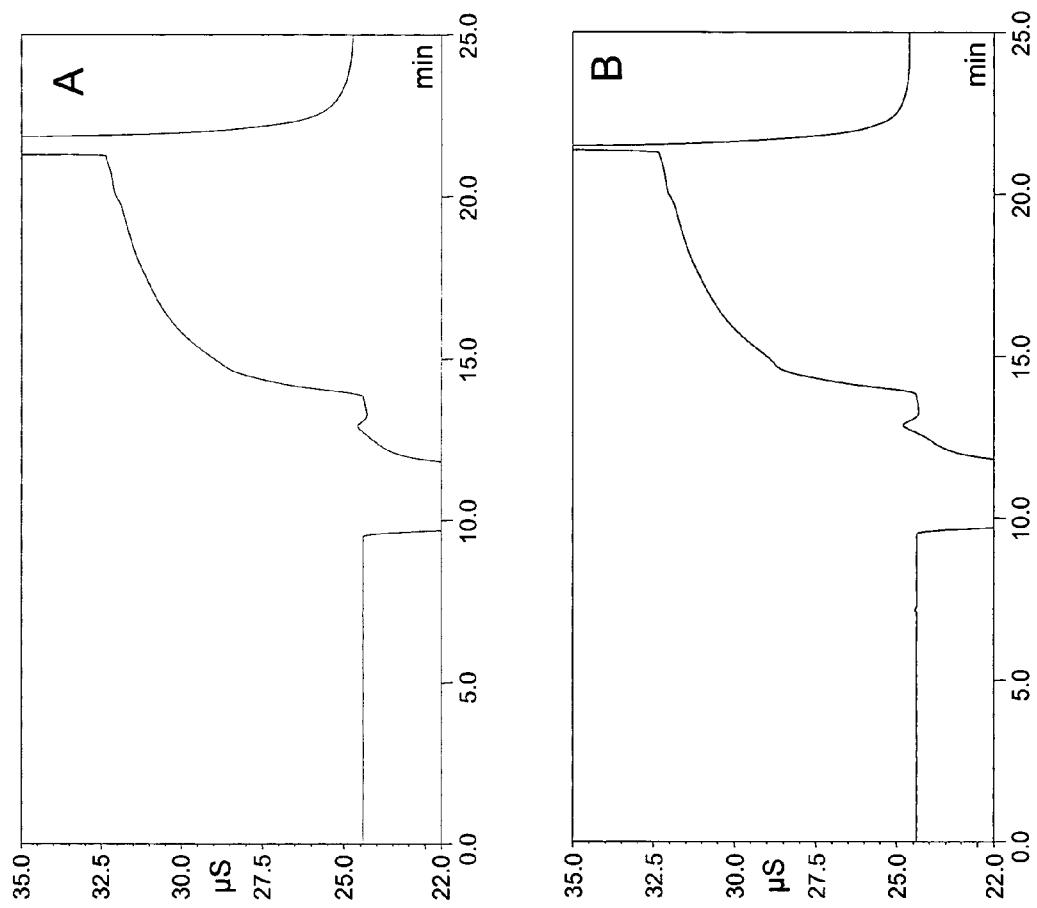
Figure 12:
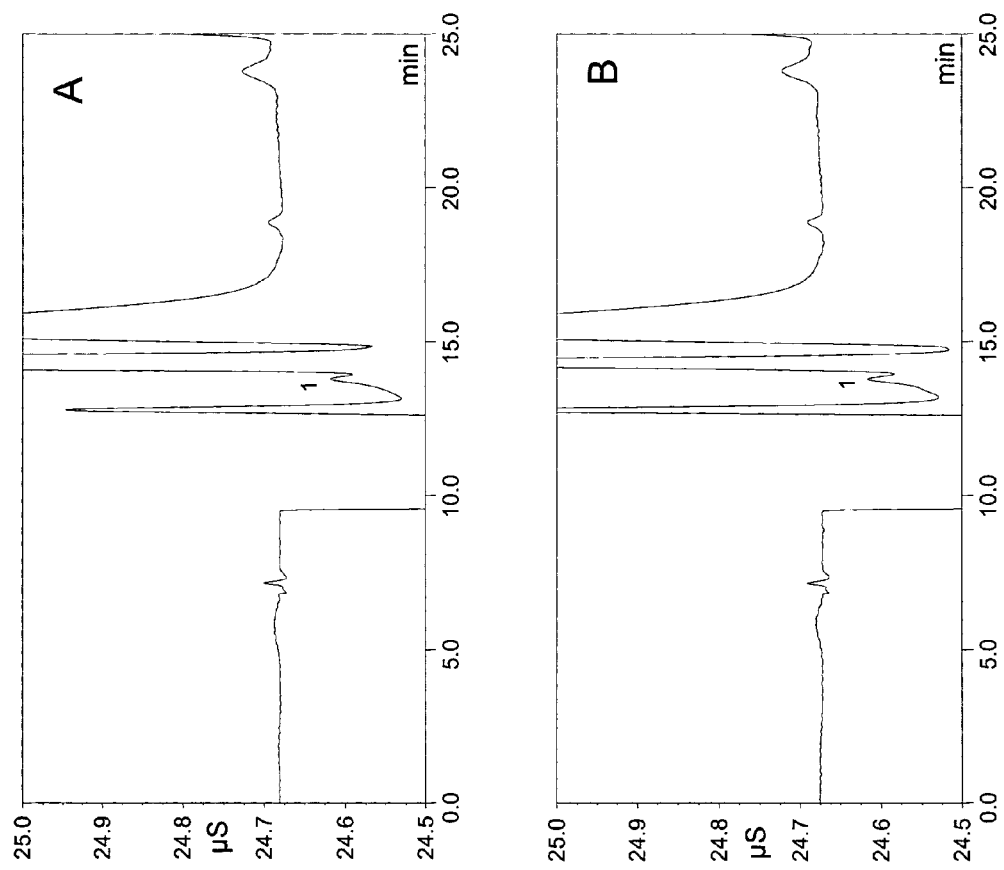

In this example, a cut volume from 4.3 to 6.8 minutes (2.5 ml) comprising the bromate peak was concentrated on a concentrator column and analyzed using a 2 mm AS9HC column operated at 0.25 ml/min flow rate. It is clear that the presence of carbonic acid interferes with the analysis as shown in FIG. 11 and the bromate peak is not detected under these conditions for a sample with (Inset A) and without (Inset B) added matrix (100 ppm of chloride and sulfate) ions. When a CRD device was installed as per the present invention between the suppressor and the concentrator column in the first dimension a significant level of $CO_2$ is removed from the cut volume resulting in improved recovery of bromate as shown in FIG. 12 (Inset A is with matrix ions and Inset B without matrix ions).

What is claimed is:

1. Ion chromatography apparatus comprising
   (a) a first housing defining a first flowthrough chamber containing first separation medium for separating ionic species of one charge, positive or negative, in a liquid sample stream,
   (b) a second housing defining a second flowthrough chamber containing second separation medium of the same charge as said first separation medium for separating ionic species in a liquid sample stream, said second chamber having a volume no greater than 0.9 times the volume of the said first chamber;
   (c) first valving disposed between said first chamber and said second chamber configured to permit selective transfer of ionic species from first chamber to second chamber for further analysis;
   (d) a flowthrough ionic species concentrator disposed in said first valving and in fluid communication therewith; said first valving having a first position in which said first chamber is in fluidic communication with said concentrator and a second position in which liquid flow from said first chamber bypasses said concentrator, said first valving permitting continuous flow through said first chamber in both said first position and said second position.

2. The apparatus of claim 1 further comprising
   (e) first suppressor in fluid communication with said first flowthrough chamber downstream from said first chamber and upstream from said second chamber.

3. The apparatus of claim 2 further comprising
   (f) a first detector disposed downstream from said first suppressor but upstream from said second chamber.

4. The apparatus of claim 3 in which said first suppressor is a membrane suppressor with a membrane separating a liquid sample flow channel, in fluidic communication with said first chamber, from a first regenerant flow channel, said apparatus further comprising
   (g) a first fluid conduit between said first detector and said first regenerant flow channel.

5. The apparatus of claim 3 further comprising a second detector downstream from said second flowthrough chamber and in fluid communication therewith.

6. The apparatus of claim 5 further comprising
   (f) a second suppressor disposed between said second chamber and said second detector.

7. The apparatus of claim 6 in which said second suppressor is a membrane suppressor with a membrane separating a liquid sample flow channel, in fluidic communication with said second chamber, from a second regenerant flow channel, said apparatus further comprising
   (g) a fluid conduit between said second detector and said second regenerant flow channel.

8. The apparatus of claim 1 further comprising
   (e) a gas removal device disposed between said first flowthrough chamber and said concentrator column.

9. The apparatus of claim 1 further comprising a first pump upstream of said first chamber for pumping liquid through said first chamber, and a second pump downstream from said first chamber and upstream from said second chamber for pumping liquid through said second chamber.

10. The apparatus of claim 1 further comprising
    (e) an electrolytic eluent generator in fluid communication with the upstream side of said first chamber.

11. An ion chromatography method comprising
    (a) flowing an eluent-containing liquid sample stream containing ionic species of one charge, positive or negative, from a sample injector through a first separation medium in a first flowthrough chamber to separate said ionic species,
(b) flowing an eluent along with a selected portion of said separated ionic species from said first separation medium through a valve and a second separation medium of the same charge, positive or negative, as said first separation medium in a second flowthrough chamber to further separate said ionic species, the volumetric flow rate through said second separation medium being not more than 0.9 times the volumetric flow rate through said first separation medium, wherein the sensitivity of separation in said second separation medium is higher than the sensitivity of separation in said first separation medium,
(c) detecting in a first flowthrough detector the further separated ionic species in the aqueous liquid stream exiting from said second separation medium, and
(d) concentrating said ionic species in said sample stream exiting from said first chamber prior to flow into said second chamber, by flowing said sample stream through ionic species concentration medium in a concentrator, said eluent flowing continuously through said first chamber during steps (a)-(d).

12. The method of claim 11 further comprising
(e) suppressing the conductivity of eluent in said liquid sample stream after exiting from said first chamber and prior to flow into said second chamber.

13. The method of claim 12 in which said suppression is performed in a membrane suppressor with a permselective membrane separating a liquid sample flow channel in communication with said liquid sample stream, and a regenerant flow channel, said method further comprising
(f) detecting in a second flowthrough detector the ionic species in said sample stream exiting from said first separation chamber prior to flowing into said second chamber,
(g) flowing at least part of said liquid sample stream exiting said detector through said regenerant flow channel.

14. The method of claim 11 further comprising
(f) during step (e), flowing the aqueous solution exiting from said concentration medium to a regenerant flow channel in a membrane suppressor with a permselective membrane separating a first liquid sample flow channel in communication with said liquid sample stream, and a regenerant flow channel.

15. The method of claim 11 further comprising
(e) suppressing the conductivity of eluent in said sample stream exiting said second chamber.

16. The method of claim 15 in which said suppression is performed in a membrane suppressor with a permselective membrane separating a liquid sample flow channel in communication with the liquid sample stream exiting from said second chamber, and a regenerant flow channel, said method further comprising
(f) flowing at least part of said liquid sample stream exiting from said second chamber through said regenerant flow channel.

17. The method of claim 11 in which said second flowthrough chamber has a volume of not more than 0.9 times the volume of the first flowthrough chamber.

18. The method of claim 11 in which the cross-sectional area of the second flowthrough chamber perpendicular to flow is no greater than 0.9 times the cross sectional area of the first flowthrough chamber.

19. The method of claim 11 in which said eluent includes carbon dioxide gas, said method further comprising
(e) removing carbon dioxide gas from said sample stream upstream from said concentrator column.

20. The method of claim 11 in which the sensitivity enhancement in the second separation medium is approximately proportional to the ratio of volumetric flow rate between the first and second separation media.

* * * * *